(12) United States Patent
Kiersh et al.

(10) Patent No.: US 10,646,235 B2
(45) Date of Patent: May 12, 2020

(54) GUIDE WIRE SEAL FOR REAMER IRRIGATOR ASPIRATOR SYSTEM

(71) Applicant: DEPUY SYNTHES PRODUCTS, INC., Raynham, MA (US)

(72) Inventors: Jeff Kiersh, West Chester, PA (US); Christopher Shane, Strafford, PA (US); Sean Kerr, Oreland, PA (US); Timothy P. Moses, Raynham, MA (US)

(73) Assignee: DePuy Synthes Products, Inc., Raynham, MA (US)

( * ) Notice: Subject to any disclaimer, the term of this patent is extended or adjusted under 35 U.S.C. 154(b) by 110 days.

(21) Appl. No.: 15/794,115

(22) Filed: Oct. 26, 2017

(65) Prior Publication Data
US 2019/0125363 A1    May 2, 2019

(51) Int. Cl.
*A61B 17/00*    (2006.01)
*A61B 17/16*    (2006.01)
(Continued)

(52) U.S. Cl.
CPC ........ *A61B 17/164* (2013.01); *A61B 17/1615* (2013.01); *A61B 17/1631* (2013.01); *A61B 17/1633* (2013.01); *A61B 17/1646* (2013.01); *A61B 17/17* (2013.01); *F16C 1/107* (2013.01); *A61B 17/1635* (2013.01);
(Continued)

(58) Field of Classification Search
CPC combination set(s) only.
See application file for complete search history.

(56) References Cited

U.S. PATENT DOCUMENTS

| 5,403,317 A | 4/1995 | Bonutti |
| 5,540,707 A | 7/1996 | Ressemann et al. |

(Continued)

FOREIGN PATENT DOCUMENTS

| CN | 201701257 U | 1/2011 |
| CN | 203898409 U | 10/2014 |

(Continued)

OTHER PUBLICATIONS

Written Opinion (PCT/US2018/057624) dated Jul. 23, 2019, 14 pages.

(Continued)

*Primary Examiner* — Sameh R Boles
(74) *Attorney, Agent, or Firm* — Wayne C. Jaeschke, Jr.

(57) ABSTRACT

A system for reaming a medullary canal of a bone, comprises a reamer device including an elongated member and a reamer head rotatably coupled to a distal end of the elongated member and a drive shaft sized and shaped to be inserted through the elongated member so that a first connector at a distal end of the drive shaft is engagable with the reamer head, rotation of the drive shaft rotates the reamer head relative to the elongated member, the drive shaft including a channel extending longitudinally therethrough and a hole extending laterally therethrough from a first opening through a first side wall of the drive shaft to a second opening through a second side wall of the drive shaft in combination with a seal configured to be inserted through the hole of the drive shaft so that the seal extends across the channel of the drive shaft.

20 Claims, 10 Drawing Sheets

(51) Int. Cl.
*F16C 1/10* (2006.01)
*A61B 17/17* (2006.01)
*A61B 18/00* (2006.01)

(52) U.S. Cl.
CPC ... *A61B 17/1717* (2013.01); *A61B 2018/0063* (2013.01); *A61B 2217/005* (2013.01); *A61B 2217/007* (2013.01)

(56) References Cited

U.S. PATENT DOCUMENTS

| | | | |
|---|---|---|---|
| 5,694,951 | A | 12/1997 | Bonutti |
| 5,695,468 | A | 12/1997 | Lafontaine et al. |
| 6,022,354 | A | 2/2000 | Mercuri et al. |
| 6,024,729 | A | 2/2000 | Dehdashtian et al. |
| 6,174,313 | B1 | 1/2001 | Bonutti |
| 6,231,543 | B1 | 5/2001 | Hegde et al. |
| 6,332,886 | B1 | 12/2001 | Green et al. |
| 6,387,070 | B1 | 5/2002 | Marino et al. |
| 6,543,455 | B2 | 4/2003 | Bonutti |
| 6,565,588 | B1 | 5/2003 | Clement et al. |
| 6,648,854 | B1 | 11/2003 | Patterson et al. |
| 6,783,533 | B2 | 8/2004 | Green et al. |
| 7,081,123 | B2 | 7/2006 | Merboth et al. |
| 7,198,632 | B2 | 4/2007 | Lim et al. |
| 7,204,810 | B2 | 4/2007 | Hynes et al. |
| 7,214,059 | B2 | 5/2007 | Takahashi |
| 7,462,181 | B2 | 12/2008 | Kraft et al. |
| 7,497,340 | B2 | 3/2009 | Hershberger et al. |
| 7,771,445 | B2 | 8/2010 | Heitzmann et al. |
| 8,002,733 | B2 | 8/2011 | Kraft et al. |
| 8,043,253 | B2 | 10/2011 | Kraft et al. |
| 8,088,291 | B2 | 1/2012 | Hershberger et al. |
| 8,109,919 | B2 | 2/2012 | Kraft et al. |
| 8,622,953 | B2 | 1/2014 | Hynes et al. |
| 8,740,908 | B2 | 6/2014 | Farley et al. |
| 8,790,321 | B2 | 7/2014 | Segina et al. |
| 8,790,349 | B2 | 7/2014 | Takahashi |
| 8,920,393 | B2 | 12/2014 | Hensler et al. |
| 9,005,163 | B2 | 4/2015 | Bonnette et al. |
| 9,131,925 | B2 | 9/2015 | Kraft et al. |
| 9,555,169 | B2 | 1/2017 | Segina et al. |
| 2004/0230213 | A1 | 11/2004 | Wulfman et al. |
| 2005/0156387 | A1 | 11/2005 | Chen et al. |
| 2007/0021752 | A1 | 1/2007 | Rogers et al. |
| 2007/0276352 | A1 | 11/2007 | Crocker et al. |
| 2009/0187116 | A1 | 7/2009 | Noishiki et al. |
| 2015/0216539 | A1 | 8/2015 | Reimers et al. |
| 2015/0359998 | A1* | 12/2015 | Carmel ............... A61M 25/003 604/509 |
| 2016/0000991 | A1 | 1/2016 | Kraft et al. |
| 2016/0278790 | A1 | 9/2016 | Nassutt et al. |
| 2016/0325018 | A1 | 11/2016 | Assell et al. |
| 2017/0087349 | A1 | 3/2017 | Sutton et al. |
| 2017/0112978 | A1 | 4/2017 | Segina et al. |

FOREIGN PATENT DOCUMENTS

| | | |
|---|---|---|
| DE | 10130897 C1 | 1/2003 |
| EP | 0420395 A2 | 4/1991 |
| GB | 1458886 A | 12/1976 |
| WO | 2005096952 A1 | 10/2005 |
| WO | 2017023542 A | 2/2017 |

OTHER PUBLICATIONS

International Search Report and Written Opinion (PCT/US2018/057624) dated Jul. 15, 2019, 10 pages.

* cited by examiner

GUIDE WIRE SEAL FOR REAMER IRRIGATOR ASPIRATOR SYSTEM

BACKGROUND

Reamer Irrigator Aspirator (MA) systems are used to ream and remove material from a medullary canal of a bone such as, for example, a femur. Material from the medullary canal may be removed to prepare the bone for an intramedullary implant and/or to collect bone material for bone grafting treatments. The RIA system reams a bone while simultaneously providing irrigation and aspiration of the medullary canal. Irrigation reduces heat generated by the reamer device and emulsifies the reamed bone material. Aspiration removes the emulsified bone material from the medullary canal via a negative pressure applied through the MA system.

SUMMARY

The present embodiments are directed to a system for reaming a medullary canal of a bone, comprising a reamer device including an elongated member and a reamer head rotatably coupled to a distal end of the elongated member, the elongated member including a lumen extending therethrough and a drive shaft sized and shaped to be inserted through the lumen of the elongated member so that a first connector at a distal end of the drive shaft is engagable with the reamer head, the drive shaft extending longitudinally from a proximal end coupleable to a driving tool to the distal end including the first connector so that rotation of the drive shaft via the driving tool rotates the reamer head relative to the elongated member, the drive shaft including a channel extending longitudinally therethrough and a hole extending laterally therethrough from a first opening through a first side wall of the drive shaft to a second opening through a second side wall opposite the first side wall in combination with a seal configured to be inserted through the hole of the drive shaft so that the seal extends across the channel of the drive shaft to permit passage of a guide wire therethrough while preventing fluid from flowing therepast.

BRIEF DESCRIPTION

DETAILED DESCRIPTION

The present disclosure may be further understood with reference to the following description and the appended drawings, wherein like elements are referred to with the same reference numerals. The present embodiments relate to the treatment of a bone and, in particular, relates the intramedullary reaming of a bone to remove bone material from the medullary canal of the bone. Material from the medullary canal may be removed to prepare the bone for an intramedullary implant and/or to collect material for bone grafting. Exemplary embodiments describe a drive shaft assembly configured to be connected to a reamer device to drive or rotate a reamer head of the reamer device. The drive shaft assembly includes a drive shaft inserted into the reamer device and a seal coupleable to a portion of the drive shaft so that irrigation fluid supplied to the medullary canal via the reamer device is prevented from leaking therefrom as the assembled reamer device and drive shaft assembly are moved over a guide wire in the medullary canal. The seal is configured to be coupled to the drive shaft assembly to prevent the seal from being inadvertently disengaged from the drive shaft during use. Proper connection between the drive shaft and the seal prevents damage to the seal, reducing the likelihood of leakage. It should be noted that the terms Aproximal@ and Adistal@, as used herein, are intended to refer to a direction toward (proximal) and away from (distal) a user of the device.

As shown in FIGS. 1-8, a system 100 according to an exemplary embodiment of the present disclosure comprises a reamer device 102 including a rotatable reamer head 104 sized and shaped to be inserted into a medullary canal of a long bone (e.g., femur) to ream and remove material from the medullary canal. The reamer device 102 is configured to provide both irrigation and aspiration to the medullary canal while the medullary canal is being reamed to reduce heat generated by the reamer device 102 and to aid in the removal of material from the medullary canal. A drive shaft assembly 106 is coupleable to the reamer device 102 and a driving tool (not shown) to drive (i.e., rotate) the reamer head 104. The drive shaft assembly 106 may be coupled to the reamer device 102 by inserting a drive shaft 108 of the drive shaft assembly 106 into the reamer device 102 to couple a distal end 110 of the drive shaft 108 to the reamer head 104. A proximal end 112 of the drive shaft 108 is then coupled to the driving tool, which rotates the drive shaft 108 to rotate the reamer head 104. The assembled reamer device 102 and drive shaft assembly 106 may then be inserted into the medullary canal by sliding the assembled reamer device 102 and drive shaft assembly 106 over a guide wire 170 positioned within the medullary canal. To prevent irrigation fluid from leaking from the system 100 while also permitting the guide wire to be received therethrough, the drive shaft assembly 106 includes a seal 114 that may be positioned along a portion of the drive shaft 108. Current RIA systems include a seal mounted over a proximal end of a drive shaft, which is connected to the driving tool. In some cases, however, a proximal force of a guidewire on the seal and/or a continued longitudinal motion of the drive shaft over the guide wire disengage the seal from the proximal end of the drive shaft allowing irrigation fluid to leak and/or increasing the risk that the seal may be left behind within the patient. Thus, the seal 114 of the drive shaft assembly 106 is configured to be laterally inserted into a seal area 116 positioned along the drive shaft 108.

Figure 1:
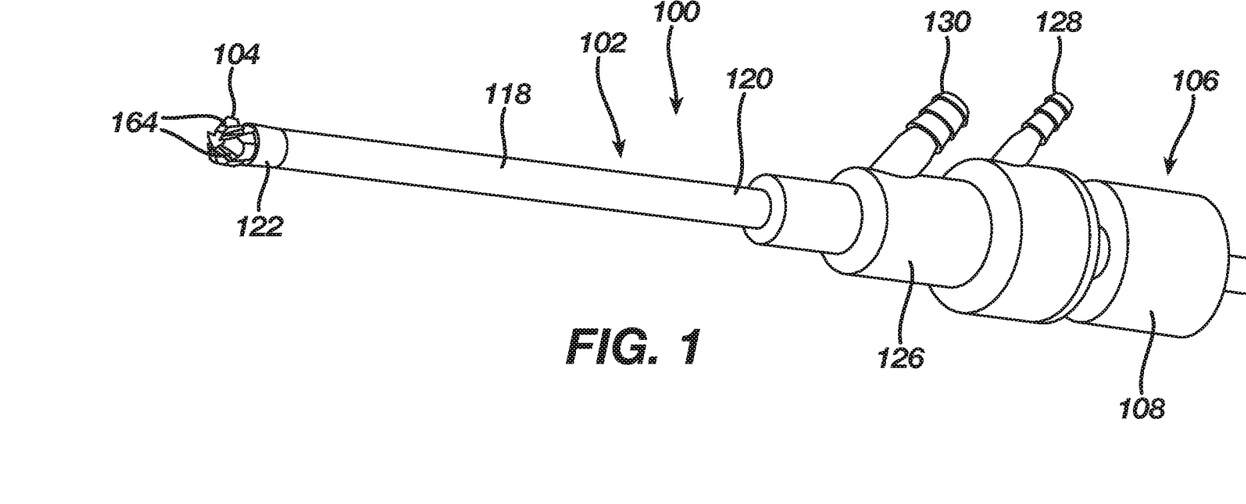
FIG. 1 shows a perspective view of a system according to an exemplary embodiment of the present disclosure.
Figure 2:
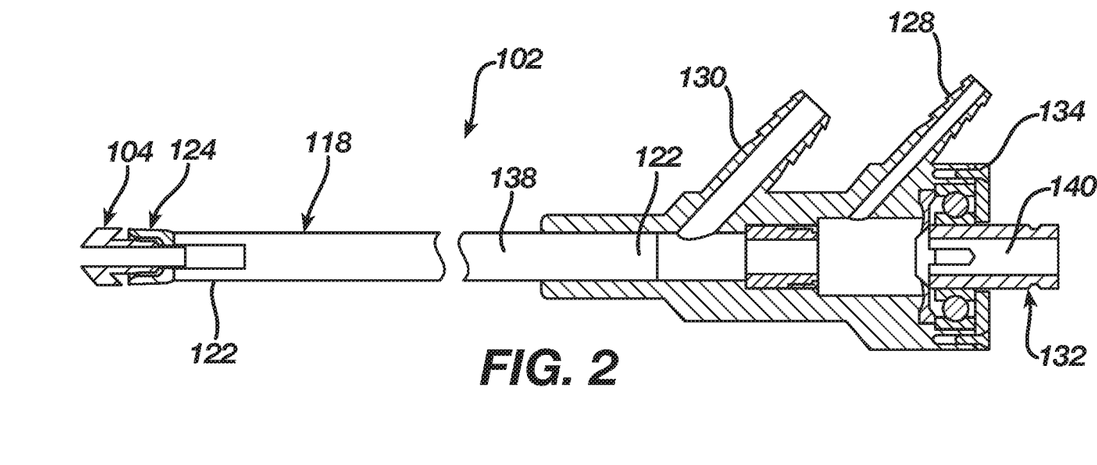
FIG. 2 shows a longitudinal cross-sectional view of a reamer device according to the system of FIG. 1.
Figure 3:
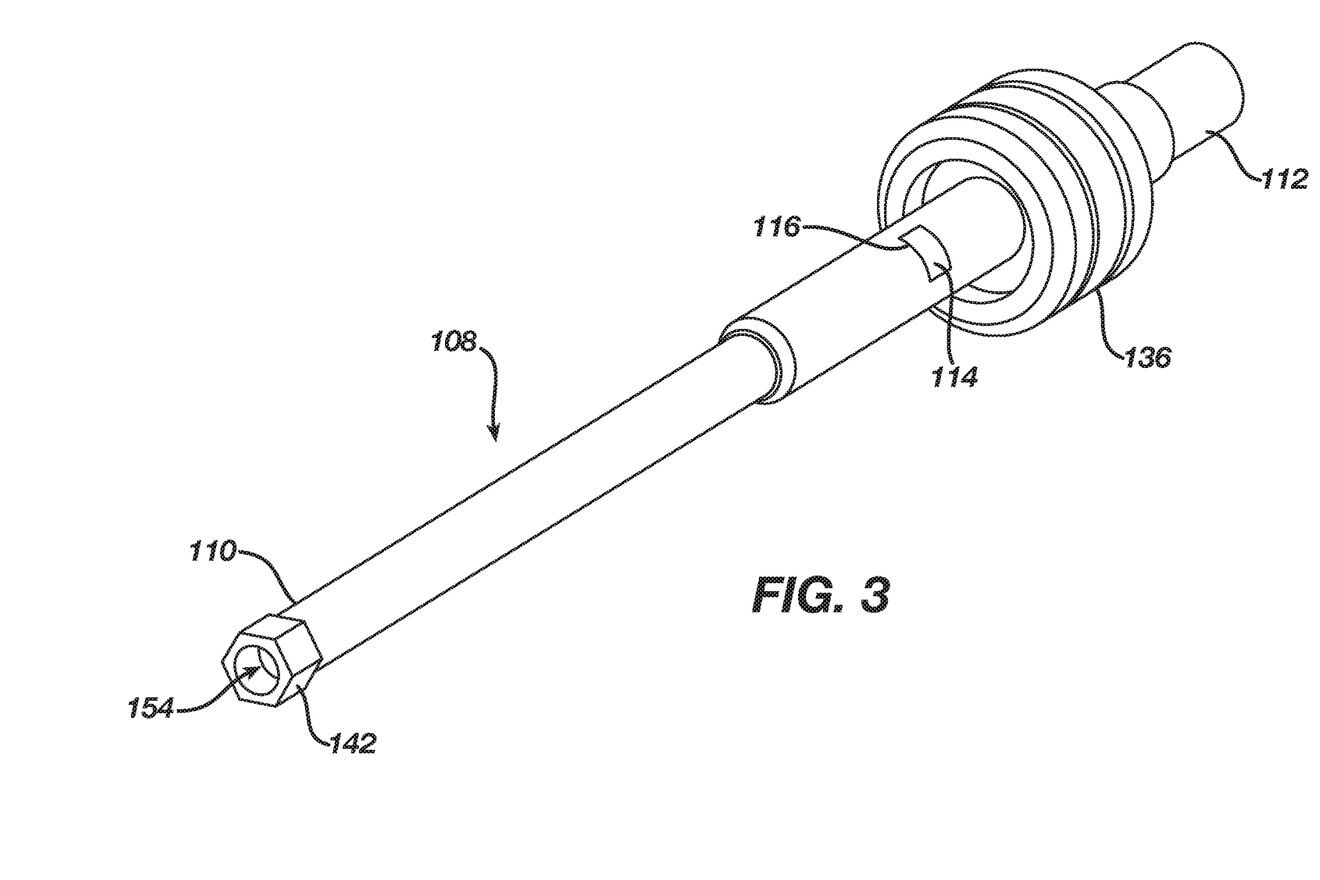
FIG. 3 shows a perspective view of a drive shaft assembly according to the system of FIG. 1.
Figure 4:
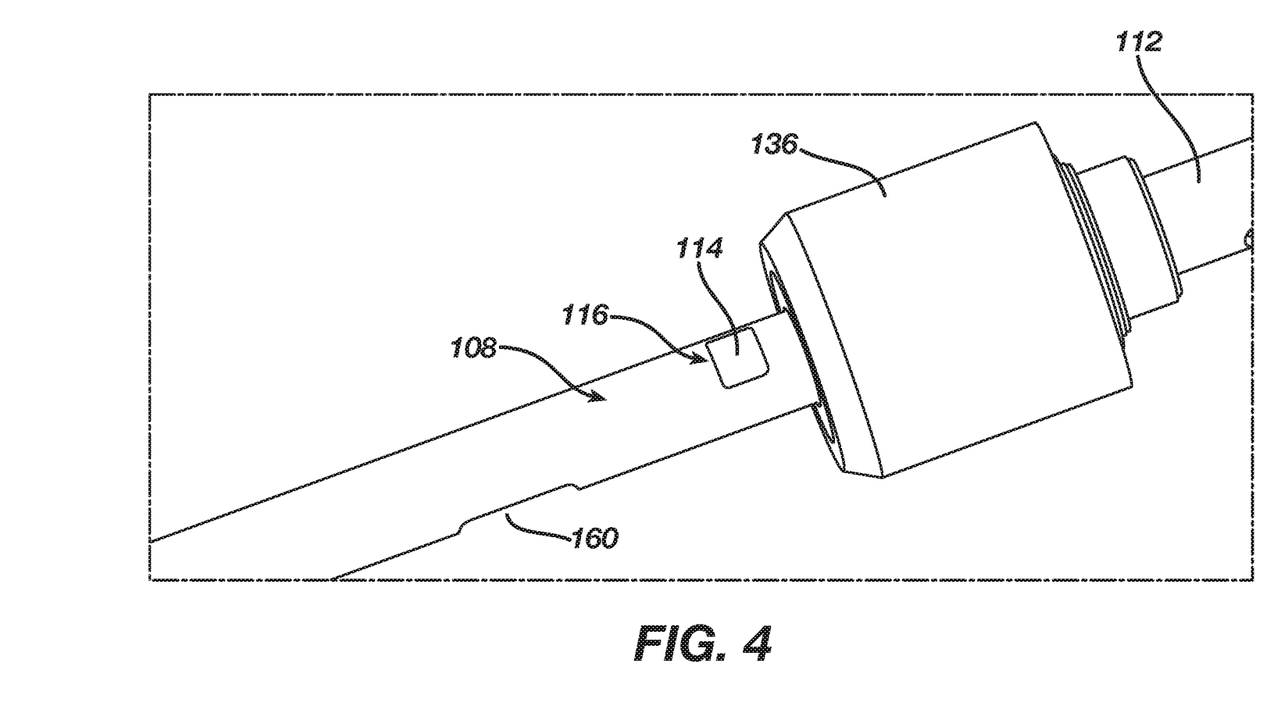
FIG. 4 shows an enlarged perspective view of a portion of the drive shaft assembly of FIG. 1.
Figure 5:
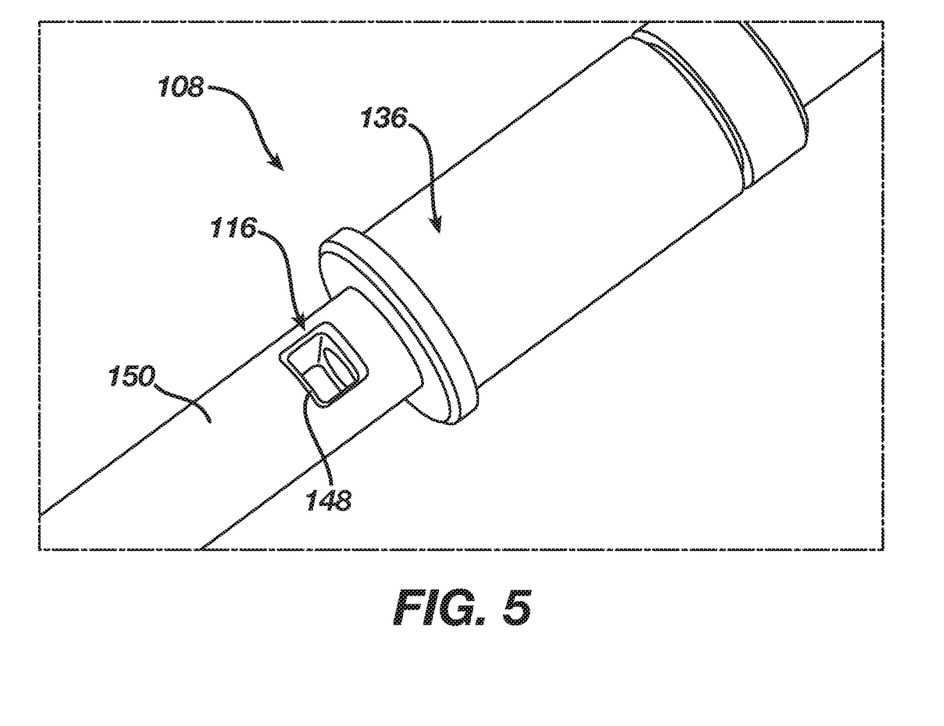
FIG. 5 shows a perspective view of a drive shaft of the drive shaft assembly of FIG. 1.
Figure 6:
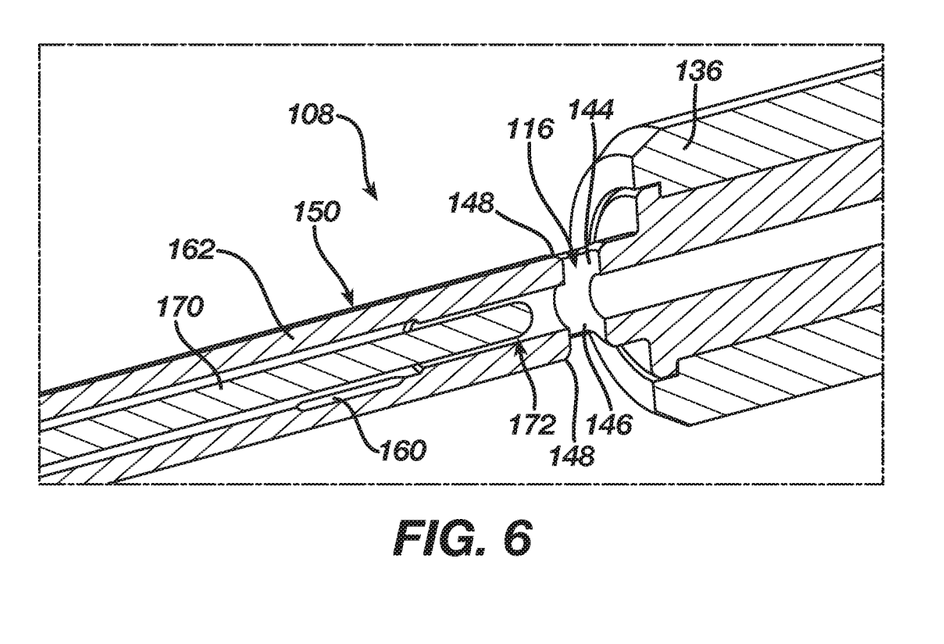
FIG. 6 shows a cross-sectional view of the drive shaft according to FIG. 1.

As shown in FIGS. 1-2, the reamer device 102 includes a tubular member 118 extending from a proximal end 120 connected to a proximal housing 126 to a distal end 122 connectable to the reamer head 104. As would be understood by those skilled in the art, the tubular member 118 is sufficiently flexible to be inserted through a medullary canal of a bone despite a curvature of the bone. The distal end 122 of the tubular member 118 is coupled to the reamer head 104 via a head connector 124. The head connector 124 allows the reamer head 104 to be rotatably coupled to the tubular member 118. In particular, the reamer head 104 is coupled to the tubular member 118 in a way that it permits the reamer head 104 to be rotated about a longitudinal axis of the reamer device 102 relative to the tubular member 118 and/or the head connector 124. The reamer head 104 includes a channel 105 extending therethrough and a plurality of blades 164 configured to ream the medullary canal as the reamer head 104 rotates relative to the flexible member 118. When the reamer head 104 is coupled to the tubular member 118/head connector 124, an axis of the channel 106 is substantially aligned with an axis of the lumen 138. The reamer head 104 further includes a plurality of openings through which irrigation fluid may be passed into the medullary canal during the reaming process. The head connector 124 also includes a plurality of openings through which aspiration is achieved as would be understood by those skilled in the art. The reamer head 104 may be releasably coupleable to the head connector 124 so that a reamer head 104 having a desired size suitable for the particular bone being treated may be selected from, for example, a plurality of heads 104 of different sizes.

The proximal housing 126 is connected to the proximal end of the tubular member 118 and includes an irrigation port 128 for connection to an irrigation fluid source, an aspiration port 130 for connection to an aspiration source and a drive shaft connector 132 at a proximal end 134 of the proximal housing 126 for connection to the drive shaft 108. Each of the irrigation and aspiration ports 128, 130 is in communication with a corresponding lumen 138 of the tubular member 118 and may include features facilitating connection with tubes for connecting to irrigation/aspiration sources. In one example, the irrigation and aspiration ports 128, 130 may include barbs. An axis along which a channel 140 of the drive shaft connector 128 extends is aligned with a longitudinal axis of the lumen 138 of the tubular member 138 so that the drive shaft 108 may be inserted into the tubular member 118 via the drive shaft connector 132. The drive shaft connector 132 includes a coupling feature for facilitating connection of the reamer device 102 and the drive shaft assembly 106.

The drive shaft assembly 106, as shown in FIGS. 3-8, includes the drive shaft 108 and the seal 114, which is laterally insertable into the seal area 116. The drive shaft 108 extends longitudinally from the proximal end 112 to a distal end 110 and includes a channel 154 extending therethrough. The drive shaft 108 also includes a reamer connection portion 136 which may be configured as an increased diameter portion of the drive shaft 108. The distal end 110 of the drive shaft 108 includes a head engaging feature 142 for engaging a corresponding feature of the reamer head 104. In one embodiment, the head engaging feature 142 includes a hex-shaped structure for engaging a correspondingly hexagonally shaped groove of the reamer head 104. Engagement between the distal end 110 of the drive shaft 108 and the reamer head 104 non-rotatably couples the drive shaft 108 to the head 104 so that rotation of the drive shaft 108 rotates the reamer head 104. A length of a portion of the drive shaft 108 extending from the reamer connection portion 136 to the distal end 110 is therefore selected to correspond to a distance from the reamer connector 132 to the reamer head 104 of the reamer device 102. In other words, when the reamer connection portion 136 is engaged with the reamer connector 132, the reamer engagement feature 142 at the distal end 110 of the drive shaft 108 must engage the corresponding engagement feature of the reamer head 104. The proximal end 112 of the drive shaft 108 may be similarly configured to be engaged to a driving tool such as, for example, a drill.

The drive shaft 108 also includes a lateral opening 160 extending laterally through a wall 162 thereof so that, when the drive shaft 108 is inserted into the reamer device 102, the lateral opening 160 is aligned with the irrigation port 128 of the proximal housing 126. Thus, irrigation fluid received through the irrigation portion 128 is passed into the channel 154 of the drive shaft 108 via the lateral opening 160 so that irrigation fluid is supplied to the medullary canal via the openings of the reamer head 104.

The seal area 116 may be configured as a hole extending laterally through the drive shaft 108 from a first wall opening 144 to a second wall opening 146 which, in this embodiment, substantially diametrically opposes the first wall opening 144. The seal area 116 is in communication with the channel 154 of the drive shaft 108. Each of the first and second wall openings 144, 146 may include beveled or angled edges 148 along an exterior surface 150 of the drive shaft 108 for engaging a lip 152 of the seal 114, as will be described in further detail below. In another embodiment, rather than beveled or angled edges, the first and second wall openings 144, 146 include a groove or recess around a periphery thereof, along the exterior surface 150. In one embodiment, the seal area may be positioned distally of the reamer connection portion 136 of the drive shaft 108 but proximally of the lateral opening 160 so that, when the drive shaft 108 is inserted into the reamer device 102, the seal area 116 is covered by a portion of the reamer device 102, preventing the seal 114 inserted therein, from being inadvertently disengaged therefrom.

Figure 7:
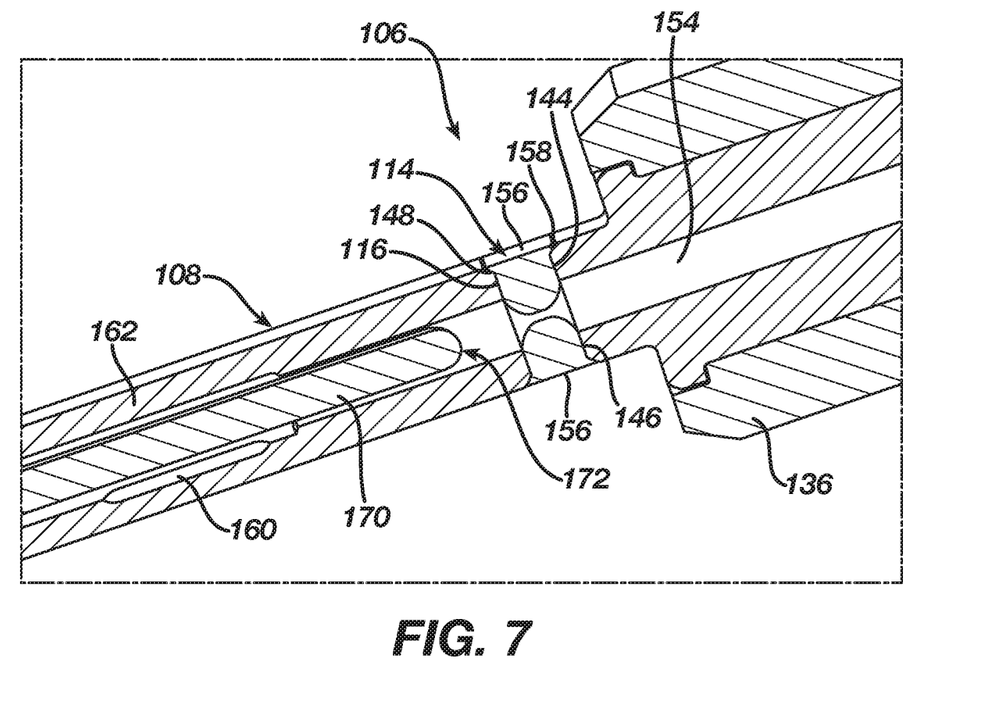
FIG. 7 shows a cross-sectional view of the drive shaft assembly of FIG. 1.
Figure 8:
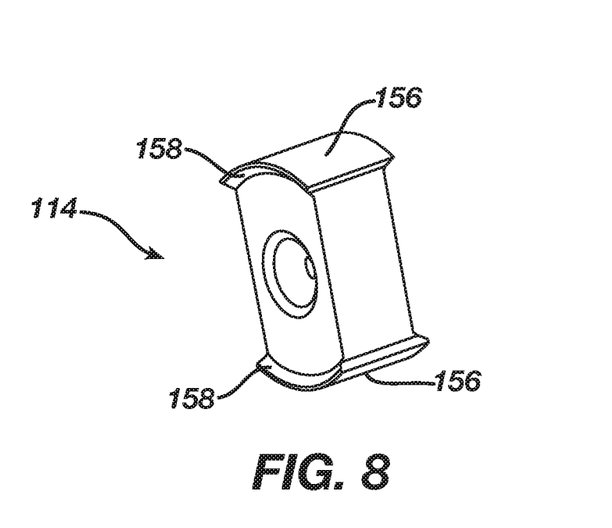
FIG. 8 shows a perspective view of a seal of the drive shaft assembly according to FIG. 1.

The seal 114 is sized and shaped to be inserted into the seal area 116 so that the seal 114 extends across the channel 154 of the drive shaft 108, covering the entire cross-sectional area of the channel 154. In one embodiment, as shown in FIGS. 7-8, the seal 114 is sized and shaped so that, when the seal 114 is inserted into the seal area 116, exterior surfaces 156 of the seal 114 are substantially flush with an exterior surface 150 of the drive shaft 108. Exterior surfaces 156 of the seal 114 may also include lips 158 (e.g., a larger cross-sectional area) for engaging the beveled edges 148 of the seal area 116. Engagement between the lips 158 and the beveled edges 148 reducing the likelihood that the seal 114 will become inadvertently disengaged from the drive shaft 108 during use. The seal 114 may have any of a variety of configurations so long as the seal 114 is insertable into the seal area 116 to seal the channel 154. For example, the seal 114 may be configured as a bivalve formed of an elastomer and/or silicone material.

According to an exemplary method for using the system 100, the drive shaft assembly 106 is assembled by inserting the seal 114 into the seal area 116 of the drive shaft 108 so that the lips 158 thereof engage the beveled edges 148 of the first and second openings 144, 146 of the seal area 116. The drive shaft 108 is then inserted into the lumen 138 of the tubular member 118 of the reamer device 102 via the drive shaft connector 132. The drive shaft 108 may be inserted into the reamer device 102 until the reamer connection 136 engages or is configured to be engaged with the drive shaft connector 132. The drive shaft connector 132 and the reamer connection portion 136 may be coupled to one another in any of a variety of ways. In one embodiment, a locking clip (not shown) is mounted over the reamer engagement portion 136 and the coupling feature of drive shaft connector 132 to lock the reamer engagement portion 136 and the drive shaft connector 132 relative to one another. An irrigation fluid source and an aspiration source (e.g., vacuum source) are also connected to the irrigation and aspiration ports 128, 130, respectively. Once the reamer device 102 and the drive shaft assembly 106 have been assembled with one another, a driving tool may be connected to the proximal end 112 to provide a rotating driving force thereto.

Prior to insertion of the reamer device 102 into the medullary canal, the bone is prepared by, for example, drilling an insertion opening into the bone and inserting the guide wire 170 into the medullary canal via the insertion opening. The reamer device 102 (assembled with the drive shaft assembly 106) is then inserted into the medullary canal over the guide wire 170 so that the guide wire 170 is received within the channel 154 of the drive shaft 108 via the channel 105 of the reamer head 104. The medullary canal is reamed while irrigation fluid is provided to the medullary canal via the irrigation port 128. Irrigation fluid flows space through the channel 154 of the drive shaft 108, around the guide wire 170, and into the medullary canal via the openings of the reamer head 104. Aspiration of tissue and/or fluids may be simultaneously provided through a space between an exterior surface 150 of the drive shaft 108 and interior of the tubular member 118 so that, for example, bone material for use in grafting may be suctioned therethrough via openings of the head connector 124.

As the reamer device 102 is slid along the guide wire 170, a proximal end 172 of the guide wire 170 is eventually pressed proximally into the seal 114, piercing the seal 114 while also preventing irrigation fluid from flowing proximally past the seal 114. As described above, the correspondingly sized and shapes seal 114 and seal area 116 along with a position of the seal area 116 distal of the reamer connection portion 136, prevents from being inadvertently dislodged or disengaged from the seal area 116, thereby reducing the likelihood of fluid leakage. Once the reaming process has been completed, the seal 114 may simply be replaced with a new seal 114 so that the same drive shaft 108 may be reused for a second reaming process.

Figure 9:
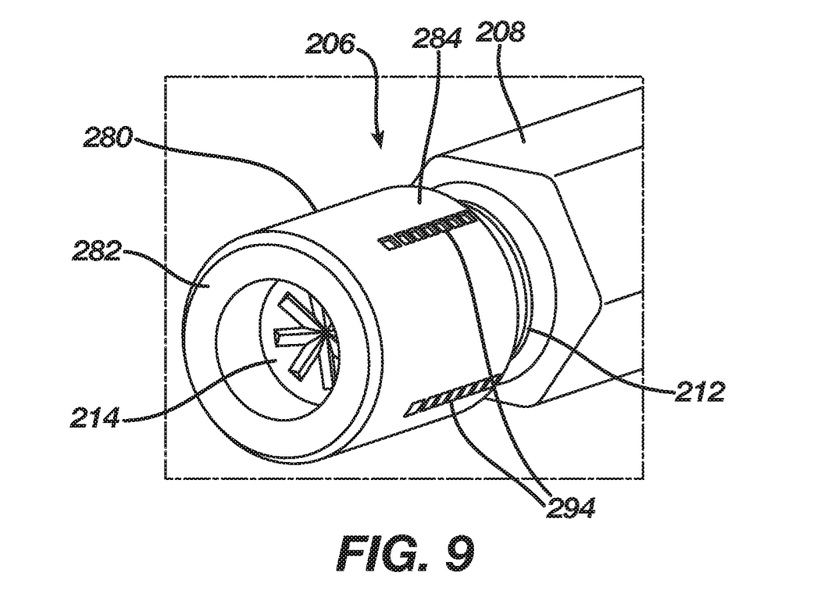
FIG. 9 shows a perspective view of a drive shaft assembly according to another exemplary embodiment of the present disclosure.
Figure 10:
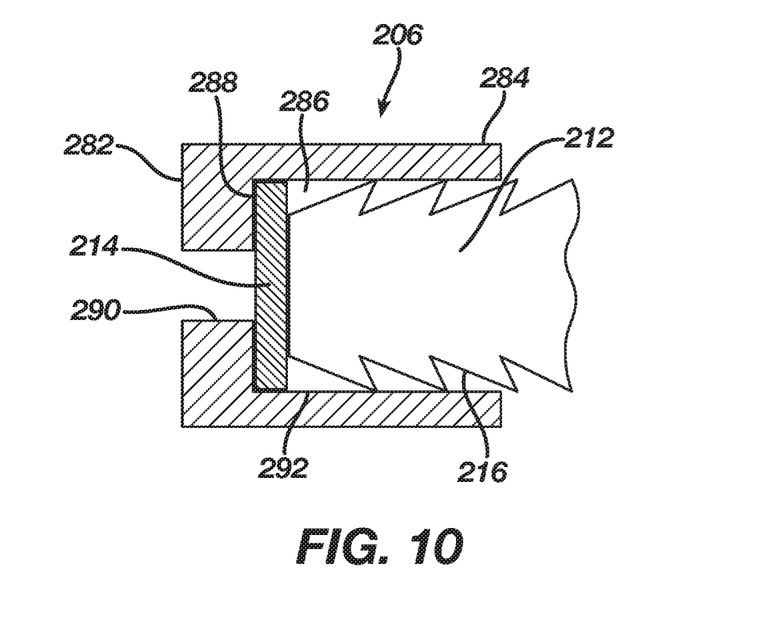
FIG. 10 shows a longitudinal cross-sectional view of the drive shaft assembly of FIG. 9.

As shown in FIGS. 9-10, a drive shaft assembly 206 according to another exemplary embodiment may be substantially similar to the drive shaft assembly 106, and may be similarly utilized with the reamer device 102 described above with respect to the system 100. Rather than a seal that is laterally insertable into a seal area, as discussed above with respect to the drive shaft assembly 106, however, a drive shaft assembly 206 may include a seal 214 that is coupleable to a proximal end 212 of a drive shaft 208 via a carrier 280 formed of, for example, a hard, plastic material such as Acrylonitrile Butadiene Styrene (ABS). This carrier 280 provides a stronger engagement with the proximal end 212 of the drive shaft 208 than a rubber or elastomer seal that is directly coupled to a proximal end of a drive shaft, as is available in current MA systems. The drive shaft 208 may be substantially similar to the drive shaft 108 described above with respect to the system 100. Rather than a seal area formed via lateral openings through the drive shaft, however, the proximal end 212 of the drive shaft 208 includes barbs 216 or other coupling features for engaging the carrier 280.

The carrier 280 extends from a proximal end 282 to a distal end 284 and includes a channel 286 extending therethrough so that, when the carrier 280 is coupled to the drive shaft 208, the channel 286 is substantially aligned with a channel of the drive shaft 208. The channel 286 includes a shoulder 288 therealong which prevents the seal 214, which is received within the channel 286, from being moved proximally therepast. A cross-sectional area of a proximal portion 290 of the channel 286 proximal of the shoulder 288 is smaller than a cross-sectional are of a distal portion 292 of the channel 286 distal of the shoulder 288. The distal portion 292 is sized and shaped to receive the proximal end 212 of the drive shaft 208 therein so that the seal 214 is fixed between the shoulder 288 and the proximal end 212 of the drive shaft 208. A diameter of the distal portion 292 of the channel 286 may be smaller than a diameter of the proximal end 212 of the drive shaft 208 so that the carrier 280 is stretched thereover to engage the proximal end 212.

The carrier 280 further includes a plurality of longitudinally extending perforations 294 extending from the distal end 284 toward the proximal end 282 along a portion of a length of the carrier 280. Each of the longitudinally extending perforations 294 extend substantially parallel to a longitudinal axis of the carrier 280. When it is desired to disengage the seal 214 from the proximal end 212, the carrier 280 may be pushed distally relative to the drive shaft 208 until a distal force thereon exceeds a predetermined threshold value so that the perforations 294 break or tear, releasing the carrier 280 and thereby the seal 214, from the proximal end 212 of the drive shaft 208.

The seal 214 is sized and shaped to be received within the distal portion 292 of the channel 286. In the embodiment shown, the carrier 280 is substantially tubular, having a substantially circular cross-section. Thus, in this embodiment, the seal 214 may be substantially disk-shaped. Pressing the seal 214 against the proximal end 212 of the drive shaft 208 via the carrier 280 during engagement thereof causes the seal 214 to expand over the barbs 216 of the proximal end 212, sealing the channel of the drive shaft 208.

Figure 11:
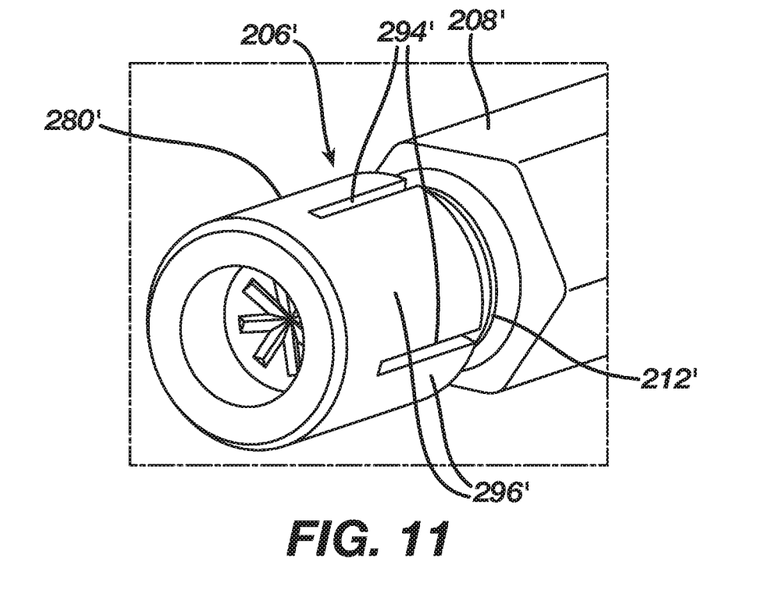
FIG. 11 shows a perspective view of a drive shaft assembly according to another exemplary embodiment of the present disclosure.
Figure 12:
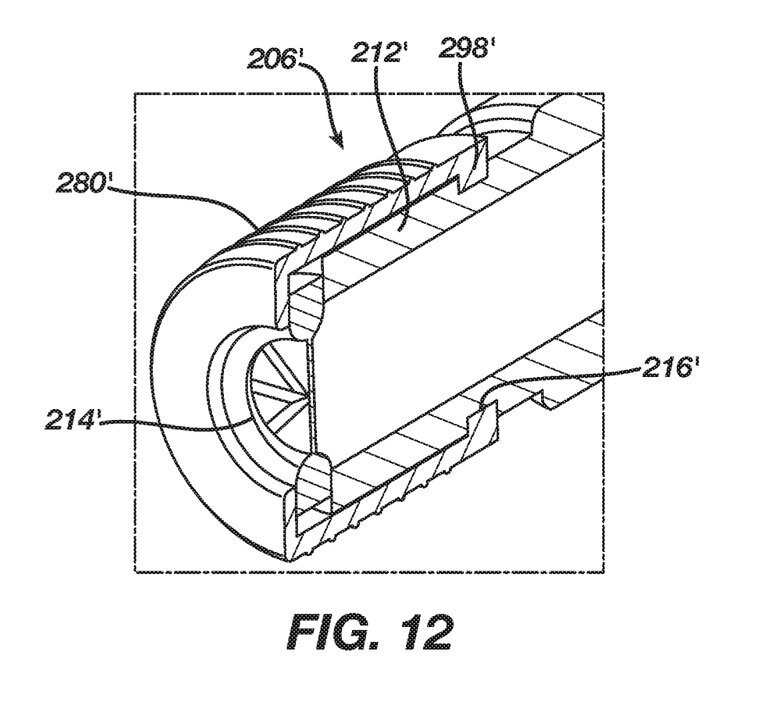
FIG. 12 shows a cross-sectional view of the drive shaft assembly of FIG. 11.

As shown in FIGS. 11-12, a drive shaft assembly 206' according to an alternate embodiment substantially similar to the drive shaft assembly 206 similarly comprises a seal 214' engaged with a proximal end 212' of a drive shaft 208' via a carrier 280'. Rather than barbs for engaging the carrier 280', however, the carrier 280' and the proximal end 212' include corresponding engaging features such as, for example, a circumferential notch 216' about the proximal end 212', which is sized and shaped to receive a correspondingly sized and shaped radially inwardly projecting tabs 298' at the distal end 284' of the carrier 280'. In addition, in place of the plurality of longitudinally extending perforations 294, the carrier 280' includes a plurality of longitudinal slots 294', which define distal arm segments 296'. These distal arm segments 296' may be movable from a first biased configuration to a second radially outwardly deflected configuration as the carrier 280' is pushed into a locked configuration along the proximal end 212'. Once the tabs 298' are received within the notch 216', the arm segments 296' revert to their initial biased configuration, fixing the carrier 280' to the proximal end 212'. Thus, when it is desired to disengage the carrier 280' from the proximal end 212', pushing the carrier 280' distally against the proximal end 212' beyond a predetermined threshold value causes the arm segments 296' to break and/or permanently deform to release the carrier 280' from the drive shaft 208'.

Figure 13:
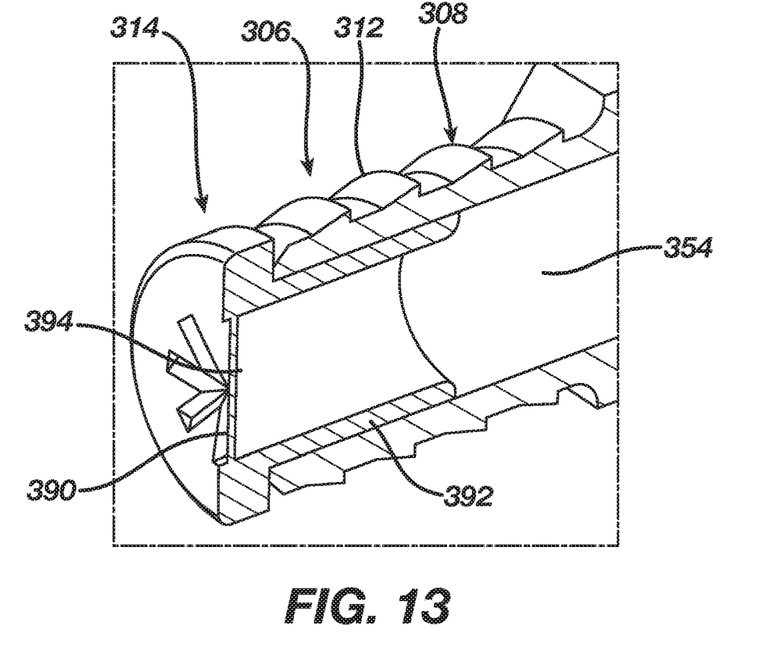
FIG. 13 shows a perspective view of yet another exemplary embodiment of the present disclosure.

As shown in FIG. 13, a drive shaft assembly 306 according to another exemplary embodiment may be substantially similar to the drive shaft assemblies 206, 206'. The drive shaft assembly 306, however comprises a seal 314 configured to be directly coupled to a proximal end 312 of a drive shaft 308. In particular, the seal 314 includes a distal portion 392 sized to be received within a channel 354 of the proximal end 312 and a proximal portion 390 formed of a soft polymer extending across a proximal opening 394 of the distal portion 392. The proximal portion 390 is configured to be pierced or broken via a guide wire passing therethrough, but is formed of material which may be compressed over the guide wired to prevent leaks thereabout.

Figure 14:
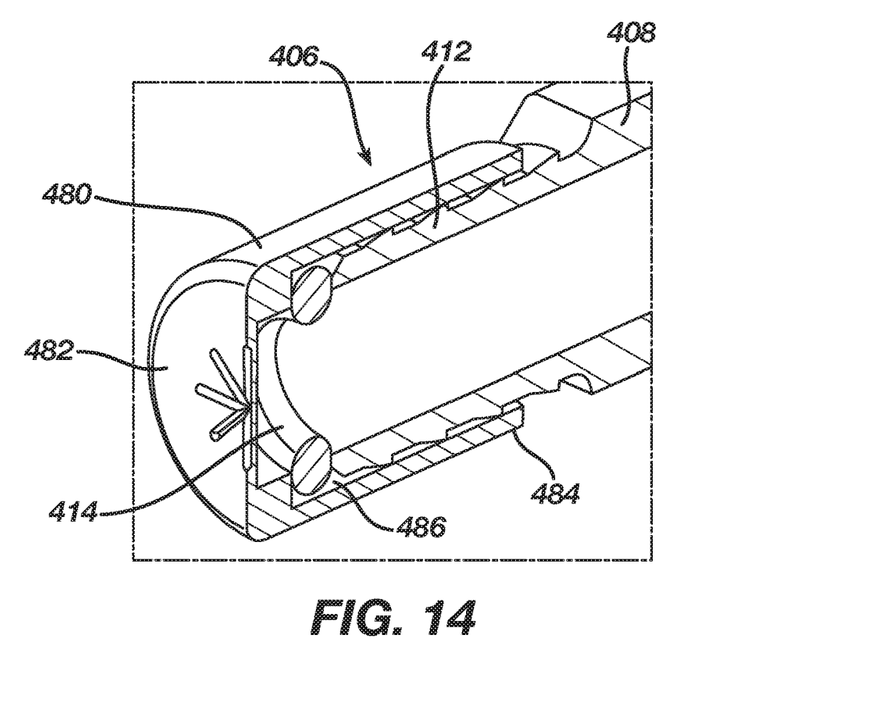
FIG. 14 shows a perspective view of another exemplary embodiment of the present disclosure.
Figure 15:
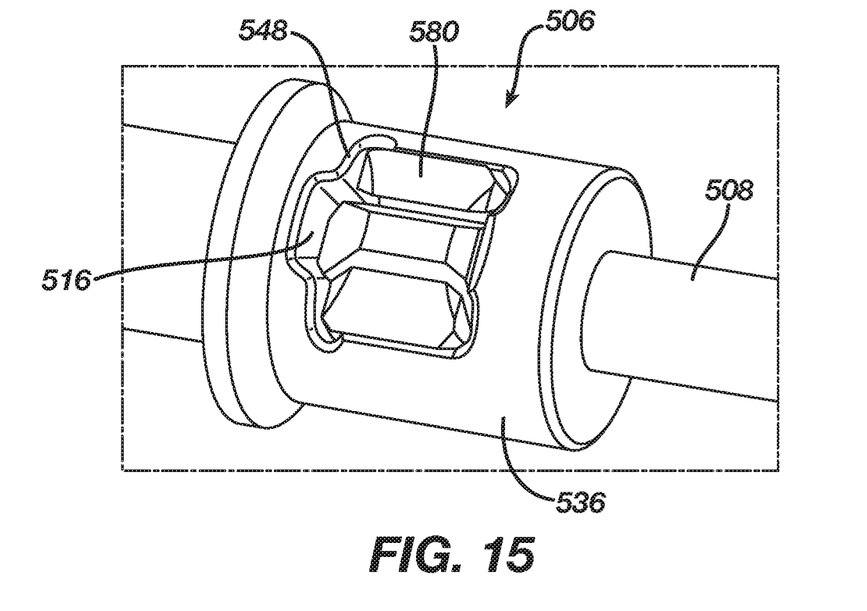
FIG. 15 shows a perspective view of yet another exemplary embodiment of the present disclosure.
Figure 16:
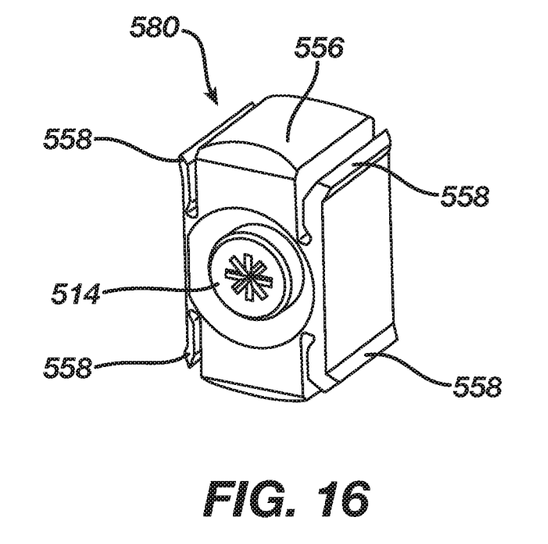
FIG. 16 shows a perspective view of a carrier and seal of the drive shaft assembly according to FIG. 15.
Figure 17:
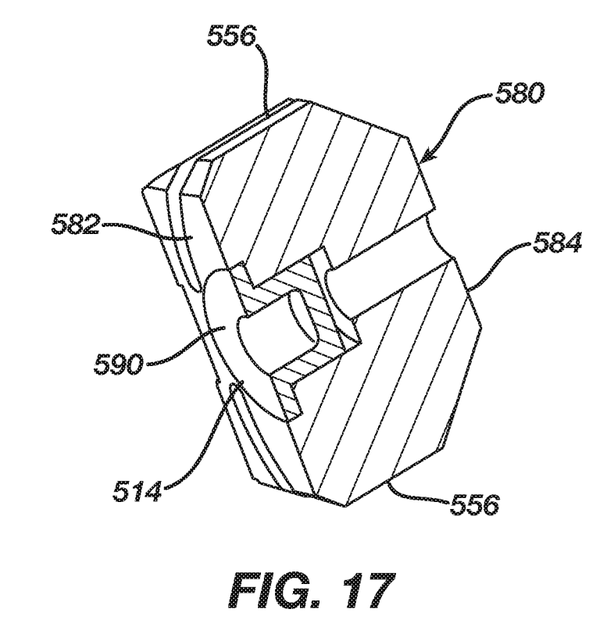
FIG. 17 shows a cross-sectional view of the carrier and seal of the drive shaft assembly of FIG. 15.
Figure 18:
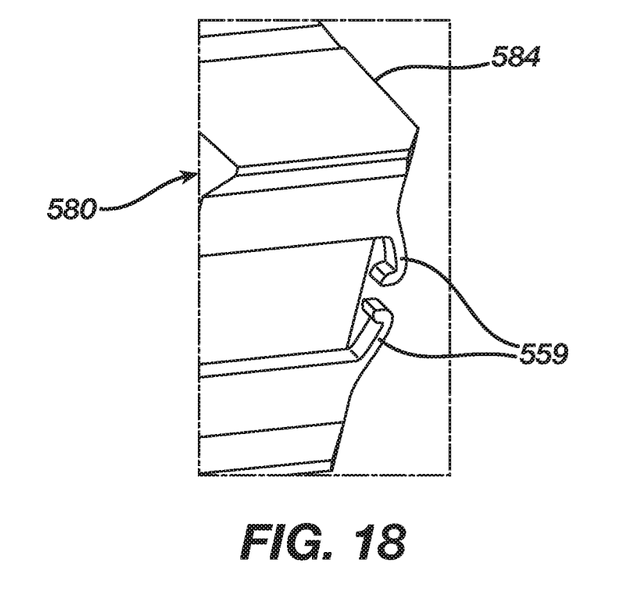
FIG. 18 shows a perspective view of a portion of the carrier of the drive shaft assembly of FIG. 15.

A drive shaft assembly 406 according to another exemplary embodiment, as shown in FIG. 14, may be substantially similar to the drive shaft assemblies 206-306 described above. The drive shaft assembly 406, however, includes a carrier 480 for fixing an O-ring 414, between a proximal end 412 of the shaft 408 and the carrier 480. The carrier 480 may be substantially similar to the carrier 280 described above with respect to the drive shaft assembly 206. A channel 486, however extends from an opening at a distal end 484 of the carrier 480 to a closed proximal end 482. The proximal end 482 is configured to be broken via passage of a guide wire therethrough. Before the guide wire passes proximally through the proximal end 482, however, the guide wire is inserted through the O-ring 414 which seals against an exterior surface of the guide wire to prevent passage of fluid thereabout.

As shown in FIGS. 15-18, a drive shaft assembly 506 according to another exemplary embodiment may be substantially similar to the drive shaft assemblies described above. In particular, similarly to the drive shaft assembles 206-406 described above, the drive shaft assembly 506 includes a carrier 580 for fixing a seal 514 to a drive shaft 508. The carrier 580, which includes the seal 514 mounted therein, however, is laterally inserted into a seal area 516, substantially similarly to the drive shaft assembly 106, as described above with respect to the system 100.

The drive shaft 508 is substantially similar to the drive shaft 108, including a seal area 516 defined via a hole extending laterally therethrough from a first wall opening 544 to a second wall opening (not shown). The seal area 516 is open to and in communication with a channel of the drive shaft 508. The seal area 516, however may extend through a reamer connecting portion 536, which may be configured as an increased diameter portion of the drive shaft 508. The seal area 516 is sized and shaped to receive the carrier 580 therein. Similarly to the seal area 116, exterior edges 548 (e.g., edges of the seal area 516 along an exterior surface of the drive shaft 508) of the first and second openings 544 may be beveled, angled and/or may include a groove extending about a periphery thereof for engaging biasing elements 558 of the carrier 580.

The carrier 580 is sized and shaped to be received within the seal area 516 and houses the seal 514 therein so that, when the carrier 580 engages the seal area 516, the seal 514 is aligned within the channel of the drive shaft 508. The carrier 580 may be sized and shaped so that, when the carrier 580 engages the seal area 516, exterior surfaces 556 thereof extend substantially flush with an exterior surface 550 of the drive shaft 508. The carrier 580 may include a first set of biasing elements 558 proximate the exterior surfaces 556 of the carrier 580 so that the first set of biasing elements 558 are movable between a first configuration toward which they are biased and a second configuration in which the biasing elements 558 are deflected toward edges of the exterior surfaces 556. Thus, as the carrier 580 is being inserted laterally into the seal 516, the biasing elements 558 are moved toward the second configuration. Once the biasing elements 558 are positioned proximate the exterior edges 548 of the first and second openings 544, however, the first biasing elements 558 are permitted to revert to the first configuration (under their natural bias) to engage the edges 548 of the first and second openings 544.

The seal 514 may have any of a variety of configurations so long as the seal 514 is housed within the carrier 514 and extends across the channel of the drive shaft 508, when the carrier 580 is inserted into the seal area 516, to seal about a guide wire passed therethrough. In one particular embodiment, the seal 514 may be substantially similar to the seal 314 described above with respect to the drive shaft assembly 306.

In one embodiment a proximal end 590 of the seal 514 may substantially align with the proximal end 582 of the carrier 580. In this embodiment, the carrier 580 may further include a second biasing element 559 along a distal end 584 of the carrier 580 which, when the carrier 580 is received within the seal area 516, biases the carrier 580 toward a proximal direction. Thus, the seal 514 is further pressed against a proximal mating surface of the seal area 516 within the channel of the drive shaft 508.

It will be understood by those of skill in the art that modifications and variations may be made in the structure and methodology of the present invention, without departing from the spirit or the scope of the invention. Thus, it is intended that the present invention cover the modifications and variations of this invention, provided that they come within the scope of the appended claims and their equivalents.

What is claimed is:

1. A system for reaming a medullary canal of a bone, comprising:
    a reamer device including an elongated member and a reamer head rotatably coupled to a distal end of the elongated member, the elongated member including a lumen extending therethrough;
    a drive shaft sized and shaped to be inserted through the lumen of the elongated member so that a first connector at a distal end of the drive shaft is engagable with the reamer head, the drive shaft extending longitudinally from a proximal end coupleable to a driving tool to the distal end including the first connector so that rotation of the drive shaft via the driving tool rotates the reamer head relative to the elongated member, the drive shaft including a channel extending longitudinally therethrough and a hole extending laterally therethrough from a first opening through a first side wall of the drive shaft to a second opening through a second side wall opposite the first side wall; and a seal configured to be inserted through the hole of the drive shaft so that the seal extends across the channel of the drive shaft to permit passage of a guide wire therethrough while preventing fluid from flowing therepast.

2. The system of claim 1, wherein the drive shaft includes a second connector proximate the proximal end thereof for connection to a proximal end of the reamer device.

3. The system of claim 2, wherein the hole extends through the drive shaft distally of the second connector so that, when the drive shaft is inserted into the elongated member, the hole is covered by a portion of the reamer device.

4. The system of claim 2, wherein the second connector is defined via an increased diameter portion of the drive shaft.

5. The system of claim 4, wherein the hole extends through the increased diameter portion of the drive shaft.

6. The system of claim 1, wherein the seal is sized and shaped so that, when the seal is inserted into the hole, the seal engages the first and second openings.

7. The system of claim 1, wherein exterior surfaces of the seal are substantially flush with an exterior surface of the drive shaft.

8. The system of claim 1, wherein the seal includes a first lip along a first exterior surface and a second lip along a second exterior surface for engaging the first and second openings, respectively.

9. The system of claim 1, further comprising a carrier housing the seal, the carrier sized and shaped to be inserted through the hole so that the carrier engages the first and second openings of the hole.

10. The system of claim 9, the carrier including a first set of biasing elements configured to engage the first and second openings when the carrier is in a desired position within the hole.

11. The system of claim 9, wherein the carrier includes a second biasing element configured to engage a portion of the hole so that the seal is pressed against a proximal surface of the hole.

12. A system for reaming a medullary canal of a bone, comprising:

a reamer device including an elongated member and a reamer head rotatably coupled to a distal end of the elongated member, the elongated member including a lumen extending therethrough;

a drive shaft sized and shaped to be inserted through the lumen of the elongated member so that a connector at a distal end of the drive shaft is engagable with the reamer head, the drive shaft extending longitudinally from a proximal end coupleable to a driving tool to the distal end including the connector so that rotation of the drive shaft via the driving tool rotates the reamer head relative to the elongated member, the drive shaft further including a channel extending longitudinally therethrough; and a seal engagable with the proximal end of the drive shaft via a carrier housing the seal, the carrier mountable to the proximal end so that the seal is pressed thereagainst to permit a guidewire to be passed therethrough while preventing a fluid to flow proximally therepast.

13. The system of claim 12, wherein the carrier extends from a proximal end to a distal end and includes a channel extending therethrough, the carrier mountable over the proximal end of the drive shaft so that the seal is fixed between a shoulder of the channel of the carrier and the proximal end of the drive shaft in alignment with the channel of the drive shaft.

14. The system of claim 12, wherein the seal is substantially disc-shaped.

15. The system of claim 12, wherein the carrier includes a plurality of longitudinally extending perforations extending along a distal portion thereof so that, when the carrier is pressed distally against the drive shaft, the perforations tear to release the carrier from the proximal end of the drive shaft.

16. The system of claim 12, wherein the carrier includes a plurality of longitudinal slots extending along a distal portion thereof so that, when the carrier is pressed distally against the drive shaft, distal segments of the carrier defined via the longitudinal slots are moved radially outward to release the carrier from the proximal end.

17. The system of claim 16, wherein each of the distal segments include a tab extending radially inward for engaging a corresponding groove along the proximal end of the drive shaft when the carrier is mounted thereover.

18. The system of claim 12, wherein the carrier is integrally formed with the seal.

19. The system of claim 12, wherein a portion of the carrier is sized and shaped to be received within the proximal end of the drive shaft via a friction fit.

20. The system of claim 12, wherein the seal is configured is an O-ring sized and shaped to seal about a guidewire inserted therethrough.

* * * * *